United States Patent [19]
Knight et al.

[11] Patent Number: 5,972,355
[45] Date of Patent: Oct. 26, 1999

[54] STABLE COMPOSITIONS CONTAINING BIOLOGICALLY ACTIVE COMPONENTS

[75] Inventors: E. Althea Knight, Teaneck, N.J.; Akshay Talati, East Meadow, N.Y.; Jules Zecchino, Closter, N.J.

[73] Assignee: E-L Management Corp., New York, N.Y.

[21] Appl. No.: 08/941,182

[22] Filed: Sep. 30, 1997

[51] Int. Cl.⁶ .............................. A61K 7/00; A61K 31/70; A61K 31/07
[52] U.S. Cl. ............................ 424/401; 514/23; 514/725; 514/844; 514/938
[58] Field of Search ............................ 424/401; 514/725, 514/23, 844, 938

[56] References Cited

U.S. PATENT DOCUMENTS

| | | | |
|---|---|---|---|
| 5,453,284 | 9/1995 | Pellico . | |
| 5,484,816 | 1/1996 | Yanagida et al. | 514/725 |
| 5,607,681 | 3/1997 | Galley et al. | 424/405 |

FOREIGN PATENT DOCUMENTS

| | | | |
|---|---|---|---|
| 0 440 398 | 7/1991 | European Pat. Off. | A61K 7/48 |
| 0 450 800 | 10/1991 | European Pat. Off. . | |
| 0451 972 | 10/1991 | European Pat. Off. . | |
| WO 91/11105 | 8/1991 | WIPO . | |
| WO 92/01466 | 2/1992 | WIPO . | |
| WO 94/05252 | 3/1994 | WIPO . | |
| WO 95/26137 | 10/1995 | WIPO . | |
| WO 97/26908 | 7/1997 | WIPO . | |
| 9731620 | 9/1997 | WIPO . | |

OTHER PUBLICATIONS

Branen et al., "Antimicrobials in Foods", pp. 2–3 (Marcel Dekker, Inc., 1983).

*Primary Examiner*—Shelley A. Dodson
*Assistant Examiner*—Marina Lamm
*Attorney, Agent, or Firm*—Dorene M. Price, Esq.; Karen A. Lowney, Esq.

[57] ABSTRACT

The present invention relates to stable water-containing cosmetic or pharmaceutical compositions which comprise a biologically active agent and an enzyme-based oxygen-scavenging antioxidant system. The composition preferably comprises an antioxidant system comprising effective amounts of an oxidase, a substrate for the oxidase, and a peroxidase, and at least one species oxidizable by hydrogen peroxide, such as iodide and/or thiocyanate anions.

19 Claims, No Drawings

STABLE COMPOSITIONS CONTAINING BIOLOGICALLY ACTIVE COMPONENTS

FIELD OF THE INVENTION

The invention relates to cosmetic and pharmaceutical compositions containing biological actives. More specifically, the invention relates to water-containing compositions which are stabilized so as to prevent degradation of the biological actives.

BACKGROUND OF THE INVENTION

In recent times, cosmetics have become developed beyond the concept of mere ornamentation for the face. Consumers now demand more from their makeup than simple color, coverage or moisturizing: it is now preferred that cosmetics provide some benefit to the skin, rather than just decorating it or making it feel softer. This consumer preference has resulted in the frequent use of biologically active ingredients in many cosmetic products. In view of the now well-recognized damaging effects of sun exposure on the skin, particularly favored active components are those which can counteract or prevent those effects. These components include, for example, sunscreens, antioxidants, and anti-wrinkle agents.

One of the primary difficulties in employing actives in a formulation is the potential instability of the active once incorporated. The very reason for their use in the formulation, i.e., their biological activity, means that they are not inert, and are therefore potentially subject to reduction or complete loss of potency if not combined with the proper vehicle. A number of routinely encountered factors can readily inactivate a biologically active compound in a formulation before it even reaches the consumer. Such factors include, for example, oxygen, extreme temperatures, UV light, water, and lipid peroxidases. It is particularly difficult to avoid the effects of oxygen and UV light, which are of course virtually ubiquitous in nature. Although degradation due to water can technically be avoided by anhydrous formulation, a water-containing formula is generally a preferred delivery system, as it provides hydration to the skin. Thus, there continues to be a need for development of a cosmetically acceptable vehicle which can deliver the hydrating benefits of water, yet will protect the actives contained in the vehicle from the degrading effects of environmental factors, including water, which rob them of their biological activity. The present invention provides a solution to this continuing problem.

SUMMARY OF THE INVENTION

The present invention relates to a water-containing cosmetic or pharmaceutical composition for topical application to the skin comprising a biologically active agent and an antioxidant system which actively scavenges oxygen. Preferably this antioxidant system comprises an oxidase, a peroxidase, and a substrate for the oxidase. A particularly useful antioxidant system comprises iodide anions and thiocyanate anions in a weight:weight ratio of 0.1:1 to 50:1 and having a combined anion weight concentration of at least 5 mg/kg, D-glucose in a weight concentration of at least 0.2 g/kg, and an effective amount of glucose oxidase and a lactoperoxidase. In a particularly preferred embodiment, the biologically active agent is a retinoid.

DETAILED DESCRIPTION OF THE INVENTION

Antioxidants are frequently used in formulations for a number of reasons. Of course, a primary function of any antioxidant is to prevent oxidative degradation of the formulation containing it, by scavenging oxygen radicals in the environment. An effective antioxidant may also act to prevent or reduce microbial growth, and therefore prevent spoilage of the vehicle. Both these activities can contribute to the overall stability of the formulation. The task is greater, however, when water is present in the formulation, and further, when there is a biologically active material in the formulation. The combination of the hydrolytic activity of water with the presence of a biologically reactive molecule, without some protective measures, inevitably leads to degradation and loss of activity of the biological active. In such a case, an antioxidant alone, while potentially capable of protecting the vehicle as a whole from degradation, is rarely capable of providing adequate preservation of biological activity. The problem is particularly exacerbated in an oil-in-water vehicle, the most commonly used in skin-care compositions. There is apparently significant diffusion of oxygen at the water-oil interface in such a system, potentially resulting in a serious degradation problem even for sensitive actives encapsulated in the oil phase.

It has now been surprisingly discovered that a specific type of antioxidant system, which actively scavenge oxygen molecules in the medium, can be highly effective in preventing loss of activity of biological materials even in the difficult environment of an oil-in-water emulsion. This type of antioxidant differs from more standard antioxidants, for example, BHT, BHA, propyl gallate, tocopherol, ascorbic acid, and the like, which cannot actively eliminate the damaging oxygen radicals from the medium in which they are contained. To achieve the oxygen-scavenging activity, the antioxidant system is enzyme-based. A preferred system is one which comprises as its basic elements an oxidase, a peroxidase, and a substrate for the oxidase. These components are elements of naturally-occurring physiological pathways in the body, and therefore, the antioxidant system provides the added advantage of being a truly natural preservative.

The oxidase in the system is one which catalyzes the production of $H_2O_2$ by the oxidation of a substrate in the presence of water and oxygen. Examples of useful oxidases for this purpose are glucose oxidase or galactose oxidase. Appropriate substrates for these enzymes are respectively, D-glucose or galactose, or precursors of these compounds, for example oligomers or polymers that can break down into the smaller sugar units. The amount of oxidase used is preferably at least about 25 U/kg of the total composition, a unit being defined herein as the amount of enzyme required to catalyze the transformation of 1.0 micromole of substrate per minute at 25° C. under optimal conditions. More preferably the amount of oxidase is at least about 75 U/kg, and most preferably about 150 U/kg. The substrate for the oxidase is preferably provided in an amount of at least about 0.5 g/kg, preferably at least 1 g/kg, and more preferably at least 2 g/kg.

The other enzyme component of the antioxidant system is a peroxidase, i.e., an enzyme which catalyzes the oxidation of a readily oxidizable species by hydrogen peroxide within the medium. The peroxidase may be any peroxidase, for example, lactoperoxidase, myeloperoxidase, or horseradish peroxidase. The amount of peroxidase is preferably at least about 10 U/kg. It is preferred that the readily oxidizable species be provided as part of the antioxidant system. Examples of useful oxidizable species are iodide, thiocyanate or bromide anions. Particularly preferred oxidizable species are one or both of iodide and thiocyanate anions. In addition to providing a relatively innocuous reservoir for potentially damaging oxygen, the oxidized species have a strong antimicrobial activity which prevents the growth of bacteria in the vehicle. The anions are generally incorporated into the system in the form of salts, such as potassium and sodium iodide salts, or mixtures thereof, and potassium, sodium, ammonium, ferric and cuprous salts of thiocyanate, and mixtures thereof. A preferred weight concentration of iodide ions is at least 5 mg/kg and for thiocyanate, at least 2 mg/kg.

The components of the antioxidant can be added to the water-containing composition individually, or as part of a separate antioxidant mixture. A particularly useful mixture of components is available commercially under the name Myavert(Boots Company PLC). The system is disclosed, for example, in U.S. Pat. No. 5,607,681, the contents of which are incorporated herein by reference. As described therein, iodide and thiocyanate anions are present in the composition in a weight ratio within a range of from 0.1:1 to 50:1, and have a combined anion weight concentration of at least 5 mg/kg, preferably at least 10 mg/kg; D-glucose in a weight concentration of at least 0.2 g/kg; glucose oxidase in an amount of at least 150 U/kg, and at least 10 U/kg lactoperoxidase.

The combined components of the antioxidant system provide a very significant level of protection, in a water-containing system, to such readily oxygen-degraded biological actives such as retinoids. Even when encapsulated in the oil phase of a composition, these compounds exhibit rapid deterioration in the presence of water, resulting in considerable loss of biological activity. However, in the presence of the oxygen-scavenging components of the invention as described above, there is a marked improvement of the retention of activity by the retinoid, thereby demonstrating the potency of the system. In a preferred composition of the invention, the composition comprises a retinoid as the biologically active agent. By retinoid in the present context is meant Vitamin A(retinol) and any natural or synthetic analogues of Vitamin A which qualitatively exhibit the same type of activity as Vitamin A on the skin. Example of retinoids, in addition to retinol include, but are not limited to, Vitamin A acid, Vitamin A aldehyde, and Vitamin A esters. The retinoids have a wide variety of dermatological applications, including the general retardation of the effects of aging, both normal and photoaging. More specific application includes prevention and reduction of wrinkles, skin atrophy, hyperpigmentation and abnormal epidermal growths. Retinoids have also proven useful in the treatment of acne. In one preferred embodiment of the invention, therefore, the antioxidants are used to stabilize a retinoid. In such compositions, the retinoid active agent is used in an amount of from about 0.001–5%, preferably about 0.001–2%, by weight of the total composition, the amount and regimen for application of application depending on the contemplated use of the retinoid.

The oxygen-scavenging system is not limited, however, to use in stabilizing retinoids. It can be used with any biological active which is susceptible to oxidative degradation, particularly in a water-containing system. Examples of other actives with which the system is useful are Vitamin E and derivatives, glutathione, and superoxide dismutase. Improvement in stability can also be observed in water-soluble as well as oil-soluble actives.

The water-compositions of the invention can be in any form, particularly water-in-oil or oil-in-water emulsions. A particular advantage is obtained, however, when the composition is an oil-in-water emulsion, which, as explained above, presents even greater difficulties with oxidative degradation than a water-in-oil emulsion. Therefore, in a preferred embodiment, the composition is an oil-in-water emulsion containing the active agent in the oil phase.

The aqueous phase of the composition may be any cosmetically acceptable water based material, such as deionized water, or a floral water. The oil phase may be any cosmetically or pharmaceutically acceptable oil, such an oil being defined for the present purpose as any pharmaceutically or cosmetically acceptable material which is substantially insoluble in water. The oils may be volatile or non-volatile, or a mixture of both. For example, suitable volatile oils include, but are not limited to, both cyclic and linear silicones, such as cyclomethicone, octamethylcyclotetrasiloxane, and decamethylcyclopentasiloxane; or straight or branched chain hydrocarbons having from 8–20 carbon atoms, such as decane, dodecane, tridecane, tetradecane, and C8–20 isoparaffins.

Non-volatile oils include, but are not limited to, vegetable oils, such as coconut oil, jojoba oil, corn oil, sunflower oil, palm oil, soybean oil; carboxylic acid esters such as isostearyl neopentanoate, cetyl octanoate, cetyl ricinoleate, octyl palmitate, dioctyl malate, coco-dicaprylate/caprate, decyl isostearate, myristyl myristate; animal oils such as lanolin and lanolin derivatives, tallow, mink oil or cholesterol; glyceryl esters, such as glyceryl stearate, glyceryl dioleate, glyceryl distearate, glyceryl linoleate, glyceryl myristate; non-volatile silicones, such as dimethicone, dimethiconol, dimethicone copolyol, phenyl trimethicone, methicone, simethicone; and nonvolatile hydrocarbons, such as isoparaffins, squalane, or petrolatum.

The emulsions may also comprise other optional components, depending on the intended end use. These include, but are not limited to, water soluble colorants (such as FD&C Blue #1); oil soluble colorants (such as D&C Green #6); water soluble sunscreens (such as Eusolex 232); oil soluble sunscreens (such as Octyl Methoxycinnamate); particulate sunscreens (such as Zinc Oxide); antioxidants (such as BHT); chelating agents (such as Disodium EDTA); emulsion stabilizers (such as carbomer); preservatives (such as Methyl Paraben); fragrances (such as pinene); flavoring agents (such as sorbitol); humectants (such as glycerine); waterproofing agents (such as PVP/Eicosene Copolymer); water soluble film-formers (such as Hydroxypropyl methylcellulose); oil-soluble film formers (such as Hydrogenated C-9 Resin); cationic polymers (such as Polyquaternium 10); anionic polymers (such as xanthan gum); vitamins (such as Tocopherol); and the like.

The invention is further illustrated by the following non-limiting examples.

EXAMPLES

Example I

A composition according to the present invention is prepared as follows:

| Material | Weight % |
| --- | --- |
| Phase I | |
| Deionized water | 51.00 |
| Wheat Protein Stearate(Bioetica) | 0.70 |
| Disodium EDTA | 0.10 |
| Sucrose | 2.00 |
| Caffeine Powder | 0.20 |

-continued

| Material | Weight % |
|---|---|
| Phase II | |
| BHT | 0.10 |
| Isostearyl Neopentanoate | 3.00 |
| Squalane | 3.00 |
| Cetearyl glucoside | 5.00 |
| Shea butter | 5.90 |
| Phase III | |
| Cyclomethicone | 7.00 |
| Phase IV | |
| Carbomer | 0.50 |
| Deionized water | 9.50 |
| Phase V | |
| Glycerine | 2.00 |
| Green tea extract | 1.00 |
| 1,3 Butylene Glycol | 1.50 |
| Deionized water | 1.50 |
| Phase VI | |
| Triethanolamine | 0.05 |
| Deionized water | 1.95 |
| Phase VII | |
| Magnesium ascorbyl phosphate | 0.35 |
| Deionized water | 2.04 |
| Phase VIII | |
| Vitamin E | 0.20 |
| Phase IX | |
| Myavert ™ substrate(Boots) | 0.72* |
| Myavert ™ enzyme(Boots) | 0.04** |
| Phase X | |
| Green tea oil extract(LipoChemical) | 0.15 |
| Retinol (10% solution in soybean oil) | 0.50 |

*Contains: 45–55% glucose(w/v), 0.42–0.52% sodium thiocyanate(w/v), and 0.66–0.80% potassium iodide (w/v)
**Contains: 1000–1800 Units/ml lactoperoxidase, 1500–2750 Units/ml glucose oxidase To prepare the composition, Phase I components are combined in the main vessel and heated to 80° C. The Phase II ingredients are combined in an auxiliary vessel and heated to 82° C. Phase I and Phase II ingredients are then combined under homomixing and side-swipe agitation. Phase III ingredients are added to the main vessel at 65° C. Phase V and Phase IV ingredients are added sequentially to the main vessel at 50° C., and each mixed until uniform. Phase VI ingredients are added to the main vessel at 40° C. and mixed until uniform. Phase VII ingredients are added at 38° C. and mixed until uniform. Phase VIII ingredients are added at 35° C. and mixed until uniform, and then Phases IX and X are added at 30° C., and mixed until uniform.

Example II

A retinol cream containing retinol and Myavert™ as described in example 1 is tested for stability, in comparison with an identical formulation without Myavert™. The creams are tested for retention of retinol activity over a period of 8 weeks, at temperatures of 4° C., 25° C., 37° C. and 45° C. At the end of 8 weeks, the control cream without the antioxidant system showed substantially full retention of activity at 4° C. and 25° C., about 86% retention of activity at 37° C., and only 74% activity at 45° C. In contrast, the antioxidant system-containing cream retained 100% activity at 4° C. and 25° C., and 94% activity at 37° C. and 45° C., showing a greater stability of the active when formulated in the presence of the glucose oxidase and lactoperoxidase.

What we claim is:

1. A stable cosmetic or pharmaceutical oil-in-water emulsion composition comprising a labile biologically active retinoid and an enzyme-based oxygen-scavenging antioxidant system.

2. The composition of claim 1 in which the antioxidant system comprises effective amounts of an oxidase, a substrate for the oxidase, and a peroxidase.

3. The composition of claim 2 in which the antioxidant system also comprises at least one species oxidizable by hydrogen peroxide.

4. The composition of claim 1 in which the antioxidant system comprises a glucose oxidase, glucose, and a lactoperoxidase.

5. The composition of claim 4 in which the antioxidant system comprises as an oxidizable species selected from the group consisting of iodide ions, thiocyanate ions, and a combination thereof.

6. The composition of claim 5 which comprises both iodide and thiocyanate ions.

7. The composition of claim 1 in which the retinoid is retinol.

8. A cosmetic or pharmaceutical oil-in-water emulsion composition comprising an effective amount of a retinoid and an antioxidant system comprising effective amounts of an oxidase, a substrate for the oxidase, and a peroxidase.

9. The composition of claim 8 in which the antioxidant system also comprises a species oxidizable by hydrogen peroxide.

10. The composition of claim 8 in which the antioxidant system comprises glucose oxidase, glucose and lactoperoxidase.

11. The composition of claim 9 which comprises an oxidizable species selected from the group consisting of iodide ions, thiocyanate ions, and a combination thereof.

12. The composition of claim 11 which the comprises both iodide and thiocyanate ions.

13. The composition of claim 8 in which the antioxidant system comprises glucose oxidase, glucose, lactoperoxidase, and iodide and/or thiocyanate anions.

14. The composition of claim 8 in which the retinoid is retinol.

15. A cosmetic or pharmaceutical oil-in-water emulsion composition comprising retinol, and an antioxidant system comprising glucose oxidase, glucose, lactoperoxidase, and iodide and/or thiocyanate anions.

16. The composition of claim 15 which comprises iodide ions a thiocyanate ions in a weight:weight ratio of 0.1:1 to 50:1, and a combined anion weight concentration of at least about 5 mg/kg, D-glucose in a weight concentration of at least 0.2 g/kg, and an effective amount of glucose oxidase and a lactoperoxidase.

17. The composition of claim 16 in which the amount of glucose oxidase is at least about 25 U/kg, and the amount of lactoperoxidase is at least about 10 U/kg.

18. The composition of claim 17 in which the amount of glucose oxidase is at least about 150 U/kg.

19. A method of stabilizing a labile biologically active retinoid in a cosmetic or pharmaceutical water-containing composition comprising adding to said composition an enzyme-based oxygen-scavenging antioxidant system.

* * * * *